(12) United States Patent
Müller

(10) Patent No.: US 9,631,957 B2
(45) Date of Patent: Apr. 25, 2017

(54) MOVEMENT SYSTEM FOR MOVING AN OBJECT, PATIENT COUCH AND METHOD FOR OPERATING A MOVEMENT SYSTEM

(71) Applicant: Matthias Müller, Kemnath (DE)

(72) Inventor: Matthias Müller, Kemnath (DE)

(73) Assignee: Siemens Aktiengesellschaft, München (DE)

( * ) Notice: Subject to any disclaimer, the term of this patent is extended or adjusted under 35 U.S.C. 154(b) by 203 days.

(21) Appl. No.: 14/671,372

(22) Filed: Mar. 27, 2015

(65) Prior Publication Data

US 2015/0276439 A1    Oct. 1, 2015

(30) Foreign Application Priority Data

Mar. 28, 2014    (DE) ........................ 10 2014 205 842

(51) Int. Cl.
*G01D 18/00*      (2006.01)
*A61G 13/02*      (2006.01)
(Continued)

(52) U.S. Cl.
CPC ............. *G01D 18/00* (2013.01); *A61G 13/02* (2013.01); *A61B 6/0457* (2013.01); *A61B 6/547* (2013.01)

(58) Field of Classification Search
CPC ..... A47C 20/041; A61B 6/0457; A61B 6/547; A61G 7/018; A61G 2203/36;
(Continued)

(56) References Cited

U.S. PATENT DOCUMENTS

| 4,769,584 A | 9/1988 | Irigoyen et al. |
| 5,540,651 A * | 7/1996 | Risch ................... A61H 9/0021 160/392 |

(Continued)

FOREIGN PATENT DOCUMENTS

DE    19804409 A1    11/1998

OTHER PUBLICATIONS

German Office action for related German Application No. 10 2014 205 842.2, dated Nov. 18, 2014, with English Translation.

*Primary Examiner* — David A Rogers
(74) *Attorney, Agent, or Firm* — Lempia Summerfield Katz LLC

(57) ABSTRACT

A movement system includes a drive having a drive shaft, a mechanism that converts an alteration to a rotational angle of the drive shaft into an alteration to an object position, and a rotational angle sensor for detecting the alteration to the rotational angle. The movement system includes a reference sensor for emitting a reference signal when the object enters a predetermined reference volume, and a controller communicating with the rotational angle sensor and the reference sensor. The controller is configured for determining a total rotational angle from alterations to the rotational angle detected according to the reference signal and for activating the drive for rotating the drive shaft by a reference rotational angle determined as a function of a predetermined reference positional value and the total rotational angle. The movement system also includes a calibration sensor for emitting a calibration signal when the object enters a predetermined calibration volume.

18 Claims, 2 Drawing Sheets

(51) Int. Cl.
    *A61B 6/04*      (2006.01)
    *A61B 6/00*      (2006.01)
(58) Field of Classification Search
    CPC .... A61G 2203/42; A61G 7/005; A61G 7/012;
                  A61G 13/025; A61H 23/0254; A61H
                                2201/0146; G01D 18/00
    See application file for complete search history.

(56) References Cited

U.S. PATENT DOCUMENTS

| | | | |
|---|---|---|---|
| 6,194,857 B1 | 2/2001 | Stolz | |
| 7,030,509 B2* | 4/2006 | Okada | B60J 7/0573 296/223 |
| 8,350,505 B2* | 1/2013 | Krause | H02P 23/14 318/400.01 |
| 9,089,459 B2* | 7/2015 | Dindas | A61G 7/012 |
| 2008/0028824 A1* | 2/2008 | Brogardh | B25J 9/1692 73/1.75 |
| 2010/0026230 A1* | 2/2010 | Lee | G05B 19/19 318/627 |
| 2011/0001444 A1* | 1/2011 | Krause | H02P 23/14 318/400.06 |
| 2011/0083271 A1* | 4/2011 | Bhai | A61G 7/015 5/610 |
| 2012/0116591 A1* | 5/2012 | Rawls-Meehan | A47C 20/041 700/275 |
| 2012/0186019 A1* | 7/2012 | Rawls-Meehan | A47C 20/041 5/616 |
| 2015/0130586 A1* | 5/2015 | Rawls-Meehan | A47C 20/041 340/4.4 |

* cited by examiner

MOVEMENT SYSTEM FOR MOVING AN OBJECT, PATIENT COUCH AND METHOD FOR OPERATING A MOVEMENT SYSTEM

This application claims the benefit of DE 10 2014 205 842.2, filed on Mar. 28, 2014, which is hereby incorporated by reference in its entirety.

BACKGROUND

The present embodiments relate to a movement system for moving an object.

In many medical applications, the positioning of an object along a linear axis or the rotation of an object about a rotational axis plays an important role. For such applications, a high degree of positional accuracy is frequently required. As a direct detection of the position of the object is frequently complex, it is advantageous (e.g., for cost reasons) to use a rotational angle sensor on a drive shaft of a drive that is used for moving the object in order to determine a displacement or a rotation of the object and thereby indirectly a position of the object. Such rotation sensors are often provided for regulating the rotational speed of the motor.

A drawback is that the drive train between the drive and the moved object may include a plurality of transmission elements, and each of these elements incorporates certain errors, such as, for example, dimensional tolerances, reverse play or a certain capacity for expansion. Therefore, a detection of the position of the object by determining a rotational angle on the drive shaft is associated with relatively significant measuring errors. If such a detection of the position is used for positioning an object, the target position at which the object is actually located also incorporates a corresponding error relative to the reference position.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a movement system that permits a more accurate positioning of an object relative thereto is provided.

A movement system includes a calibration sensor for emitting a calibration signal when the object enters a predetermined calibration volume. The control device is configured to store the current total rotational angle or a value derived therefrom when detecting the calibration signal as calibration information. The control device is also configured to determine the reference rotational angle as a function of the calibration information.

According to one or more of the present embodiments, an additional calibration sensor is provided in order to allocate a defined total rotational angle to a defined position of the object. The zero point of the alteration to the position is already assigned to a zero value of the total rotational angle by using the reference sensor. Relative to this, the rotational angles of the drive shaft are able to be detected and/or controlled. Therefore, two defined positions of the object are assigned to two defined rotational angles of the drive shaft (e.g., the zero value and the total rotational angle when the object enters the calibration volume).

Using the mechanism of the movement system, for example, a trajectory is predetermined for the possible alterations to the position of the object. The possible alterations to the position of the object are thus limited to a degree of freedom of movement, which is coupled via the mechanism to the alteration to the rotational angle of the drive shaft. In the simplest case, the movement of the object is limited to a movement along a straight line or to a rotation about a predetermined axis. The object may, however, move along a curved path, or the alteration to the position is made up by superimposing a rotation and a linear movement of the object.

According to one or more of the present embodiments, deviations of the mechanism primarily lead to positioning errors that alter in a linear manner when the rotational angle of the drive shaft is altered. If, for example, a gear ratio factor of a gear mechanism is slightly different than assumed or, due to the tensioning force or the length of the drive belt, the factor of the gear ratio changes from a rotation of the pulley to a linear movement of the drive belt, this leads to a linear error in the position of the object. Since in the movement system according to one or more of the present embodiments, however, a reference rotational angle for positioning the object as a function of calibration information is determined, two positions of the object being detected for the determination thereof (e.g., an entry of the object into a predetermined reference volume and an entry of the object into a predetermined calibration volume), such a linear error, may be compensated for. The object may be moved into the reference position described by the reference positional value, avoiding a linear error.

A conversion factor between an alteration to the rotational angle of the drive shaft and an alteration to the position of the object may be stored in the control device. The conversion factor is exclusively corrected by the calibration information. However, such a conversion factor may be directly determined as calibration information.

The reference sensor and/or the calibration sensor may in this case be a feeler. An entry into the reference volume and/or into the calibration volume leads to an actuation of the feeler. In the movement system according to one or more of the present embodiments, therefore, particularly advantageous and simple sensors may be used, and an entry into the reference volume and/or calibration volume may nevertheless be reliably detected. Alternatively, light barriers, inductive and/or capacitive sensors, or the like may be used as reference sensors and/or calibration sensors.

An actuating element may be provided on the object or fixed relative to the object. The actuating element actuates one respective feeler when the object enters the reference volume and/or when the object enters the calibration volume. By the provision of an actuating element, a greater flexibility is possible relative to the arrangement of the reference sensor and/or the calibration sensor. If the object to be moved is, for example, the bed surface of a patient couch, an actuating element may be provided on either side of the patient couch, at the side or protruding upwardly or downwardly, which actuates the respective feeler when the reference volume and/or the calibration volume is entered.

The alteration to the position of the object may, for example, be a linear movement between a first and a second predetermined position. In this case, for example, the reference sensor and the calibration sensor may be arranged at a distance from one another that is at least half (e.g., at least two thirds) of the distance between the first position and the second position.

Alternatively, the alteration to the position of the object may be a rotation about a predetermined axis between a first angular position and a second angular position. In this case, the reference sensor and the calibration sensor, for example, may be arranged at an angular distance from one another that is at least half (e.g., at least two thirds) of the angular distance between the first angular position and the second angular position.

The control device may be configured for storing a predetermined positional value or a predetermined angular value that in each case describes the relative position of the calibration sensor to the reference sensor, and for calculating the reference rotational angle and/or the calibration information as a function of the positional value and/or the angular value.

A conversion factor between an alteration to the rotational angle of the drive shaft and an alteration to the position of the object may be calculated as calibration information. For a linear movement, the positional value in this case may be the distance between the reference sensor and the calibration sensor. As the total rotational angle of the movement system is determined from the alteration to the rotational angle detected according to the reference signal, the total rotational angle corresponds to the time when the object enters the calibration volume, to a rotational angular difference that is assigned to the distance between the reference sensor and the calibration sensor. The quotient of the positional value and the total rotational angle at the time when the object enters the calibration volume, therefore, may be stored as calibration information. Accordingly, with a movement of the object that is a rotation about a predetermined axis, an alteration to the rotational angle of the object for each alteration to the rotational angle of the drive shaft may be determined as the quotient between the angular value and the total rotational angle when the object enters the calibration volume.

The position of the object in which the object enters the reference volume is predetermined as a common reference point both for the total rotational angle and for the position of the object. Any reference positional value may be converted into an assigned total rotational angle for the drive shaft. From the current total rotational angle and the total rotational angle assigned to the reference position, a reference rotational angle, about which the drive shaft is to be rotated, may be calculated.

In order to achieve a high degree of accuracy of the movement of the object, the arrangement of the reference sensor and the calibration sensor relative to the drive and the mechanism is fixedly predetermined, and the angular value and the positional value are stored as accurately as possible in the control device.

One or more of the present embodiments further relate to a patient couch for a medical examination and/or treatment device that includes a movement system according to one or more of the present embodiments. Patient couches are frequently used in medical examination and/or treatment devices for positioning the patient relative to further devices and instruments. In this case, a high degree of positional accuracy is to be provided, which is why the use of the movement system according to one or more of the present embodiments is advantageous in a patient couch. The moved object in this case may, for example, be a bed surface for the patient.

The movement system according to one or more of the present embodiments may naturally also be used in many different ways in medical examination and/or treatment devices. Thus, for example, a radiation source and/or radiation detector may be moved by the movement system according to one or more of the present embodiments. The movement system according to one or more of the present embodiments may also be used for moving objects in a plurality of degrees of freedom of movement. For each degree of freedom of movement, a separate drive shaft and separate reference sensors and rotational angle sensors may be provided.

One or more of the present embodiments further relate to a method for operating a movement system. In the method, when fulfilling a calibration condition, the following acts are performed by the control device: activating the drive for moving the object until the object enters the reference volume; setting the total rotational angle to zero; activating the drive for moving the object until the object enters the calibration volume; and storing the current total rotational angle and/or a value derived from the total rotational angle as calibration information.

For example, a conversion factor between an alteration to the rotational angle and an alteration to the position and/or alteration to the angular position may be determined as calibration information.

The fulfillment of the calibration condition may be dependent in this case, for example, on a time interval from when the method was last carried out. For example, the method may be carried out according to one or more of the present embodiments during the course of a regular operation of a movement system on a daily, weekly or half-yearly basis or at any other time intervals. Alternatively, the method may be started, according to one or more of the present embodiments, manually in order to determine new calibration information. This may be carried out, for example, before delivering a device that includes the movement system according to one or more of the present embodiments to a customer or during after-sales service.

Alternatively, the method may be carried out during normal use of a movement system. In this case, the method according to one or more of the present embodiments may be carried out, for example, when the drive is to be activated in any case, such that an uninterrupted movement of the object is to take place so that the object moves from the reference volume into the calibration volume. The method according to one or more of the present embodiments, however, may also be carried out when a corresponding movement is interrupted and/or when the direction of movement alters repeatedly between reaching the reference volume and reaching the calibration volume.

DETAILED DESCRIPTION

Figure 1:
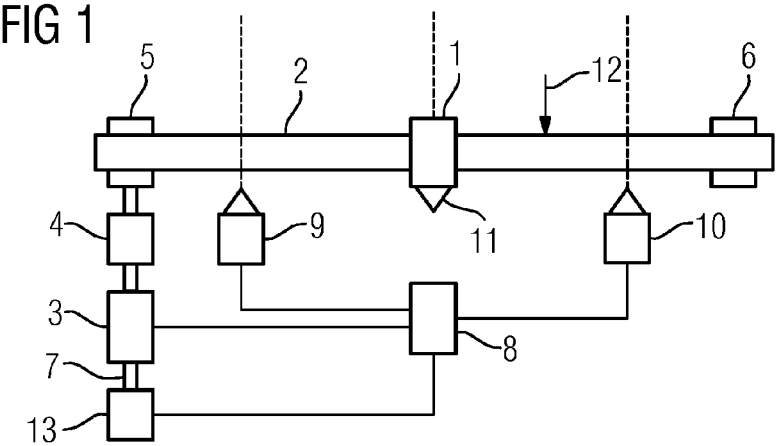
FIG. 1 shows an exemplary embodiment of a movement system.

FIG. 1 shows one embodiment of a movement system for moving an object 1. The movement of the object 1 in this case is intended to extend in a straight line. To this end, the object 1 is arranged on a drive belt 2. The movement of the object 1 is driven by a drive 3. The drive 3 has a rotating shaft 7. A mechanism is provided for converting the rotating movement of the drive shaft 7 into a linear movement. The mechanism includes a gear mechanism 4, a pulley 5, and the drive belt 2. The gear mechanism 4 translates the movement of the drive shaft 7 and transmits the movement to the pulley 5. By the rotation of the pulley 5, the drive belt 2, which is mounted on the pulley 5 and on the freely rotating roller 6, is moved in a linear manner.

By the movement system, the object 1 is now intended to be moved, for example, into the reference position marked by the arrow 12. In the movement system shown, the control device 8 controls the drive 3 in order to move the object 1 into the reference position.

Using a rotational angle sensor 8 (e.g., a rotation sensor), alterations to the rotational angle of the drive shaft are detected. In order to predetermine a common reference point for the alterations to the rotational angle of the drive shaft 7 and the position of the object 1, the control device 8 includes a reference sensor 9 that is a feeler. If the object 1 is moved into the reference region, which is adjacent to the reference sensor 9, the feeler is pushed, whereby the reference sensor 9 provides a reference signal to the control device 8. When a reference signal is received, the control device 8 sets the current total rotational angle to 0. If subsequent alterations to the rotational angle of the drive axle 7 are transmitted by the mechanism to the drive belt 2 and thus to the object 1 without slippage, each position of the object 1 may clearly be assigned a current total rotational angle detected in the control device 8.

Figure 2:
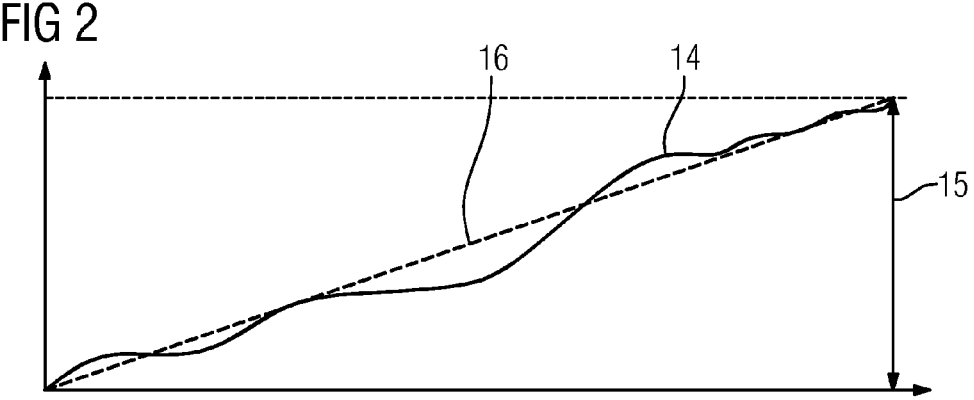
FIG. 2 shows an exemplary positioning error when the calibration sensor is not used.

In this case, the allocation between the total rotational angle and the position of the object 1 may be predetermined as a function of the specification of the mechanism, and/or the allocation between the total rotational angle and the position of the object 1 may be measured. The allocation between the total rotational angle and the position of the object 1 may be stored in the control device 8 and subsequently used for moving the object 1 to a reference position predetermined by a reference positional value. In FIG. 2, the result of such a process is shown schematically. In this case, the actual position of the object 1 in the direction of the drive belt 2 is shown on the x-axis, and the positioning error in this direction is shown on the y-axis. The positioning error is in this case the deviation of the reference positional value, which describes the reference position of the object 1 from the actual position of the object 1, after the drive 3 has been activated by the control device 8 in order to move the object 1 into the reference position. In this case, the dependence of the positioning error, shown as a curve 14, on the position at the end of the movement at a maximum distance from the reference volume, on the right-hand edge of the diagram, has a maximum error that is represented by the double arrow 15. In this case, the path of the curve 14 is relatively complex due to a plurality of deviations from the ideal behavior of the mechanism of the movement system. The positioning error, however, is characterized by a linear component that is shown by the dashed line 16. Even relatively small errors in gear ratios, as may be caused, for example, by a variation in the tension of the drive belt 2, lead to relatively large errors over the total length of the possible alteration to the position.

In order to eliminate errors that are linear when the object 1 is removed from the reference volume, the calibration sensor 10 is additionally provided in the movement system shown in FIG. 1. The calibration sensor is also configured as a feeler that is actuated by an actuating element 11 arranged on the object 1. When the object 1 enters the calibration volume and thus when an actuation of the feeler is detected by the calibration sensor 10, the calibration sensor 10 transmits a calibration signal to the control device 8. When the calibration signal is detected, the control device is able to detect the current total rotational angle (e.g., the rotational angle of the drive shaft 7 relative to the rotational angle that the drive shaft 7 had when the object 1 was in the reference volume) and is able to determine calibration information therefrom.

The distance between the reference sensor 9 and the calibration sensor 10, which are arranged fixedly relative to one another, is stored in the control device 8. When the object 1 stops in the calibration volume, the total rotational angle of the drive shaft 7 corresponds exactly to the distance between the reference sensor 9 and the calibration sensor 10. Thus a conversion factor between an alteration to the rotational angle of the drive shaft and an alteration to the position of the object 1 may be determined as calibration information (e.g., an alteration to the position in the direction of the drive belt 2).

Figure 3:
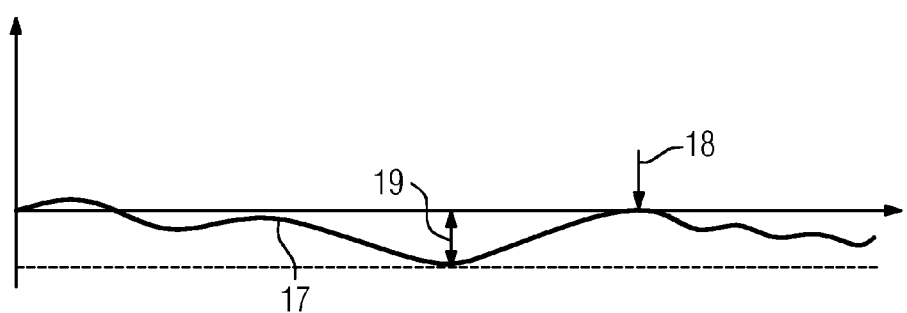
FIG. 3 shows an exemplary positioning error in the use of calibration information determined by a calibration sensor within the context of determining a reference rotational angle.

FIG. 3 shows the positioning error of the object 1 as a curve 17 in the same view as shown in FIG. 2 as the curve 14. The curve 17 shows the positioning error in the previously described use of calibration information that has been obtained by using the calibration sensor. The position of the calibration sensor 10 is indicated in FIG. 3 by the arrow 18. As a precise total rotational angle has been detected for the position of the calibration sensor 10, the positioning error for this position is equal to 0. As two positions are now predetermined with in each case predetermined total rotational angles, the error shown in FIG. 2 by the dashed line 16 is reduced to 0. Accordingly, the maximum error shown by the double arrow 19 is also much less than the maximum error shown in FIG. 2.

Using the movement system shown in FIG. 1, using relatively simple sensors (e.g., a rotational angle sensor 13 on the drive shaft 7 that is provided in many drives 3 and two further feelers), a very accurate positioning of the object 1 may be provided. As each current total rotational angle of the object may be assigned in each case with a high degree of accuracy to a position of the object, in each case, a reference rotational angle of the drive shaft 7 may also be determined from a predetermined reference positional value, as indicated, for example, by the arrow 12. By a corresponding activation of the drive 3, a corresponding reference rotational angle may be easily set by the control device 8.

Figure 4:
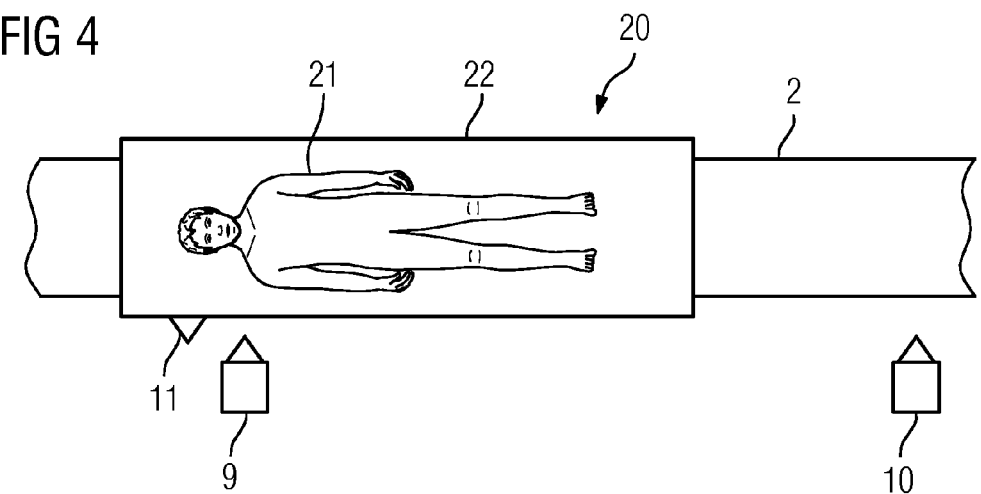
FIG. 4 shows an exemplary embodiment of a patient couch.

FIG. 4 shows one embodiment of a patient couch 20 for a medical examination and/or treatment device. The patient couch 20 serves for positioning the patient 21. The patient 21 is laid on a bed surface 22 that is movable by a drive belt 2 in one direction in order to position the patient relative to the examination and/or treatment device. In order to obtain accurate positioning of the patient 21, a movement system, as already described with reference to FIG. 1, is used. In addition to the drive belt 2, a reference sensor 9 and a calibration sensor 10 are provided in a fixed position. The sensors are configured as feelers that, during a movement of the bed 22, are actuated when the actuating element 11 sweeps thereover. In order to achieve the best possible correction of the linear error of the movement described with reference to FIG. 2 and FIG. 3, the reference sensor 9 and the calibration sensor 10 are spaced apart by approximately two thirds of the maximum movement path of the bed 22. According to the process described with reference to FIG. 1, the bed surface 22 and thus the patient 21 may be moved by a control device, not shown, to a predetermined reference position with a high degree of accuracy.

Figure 5:
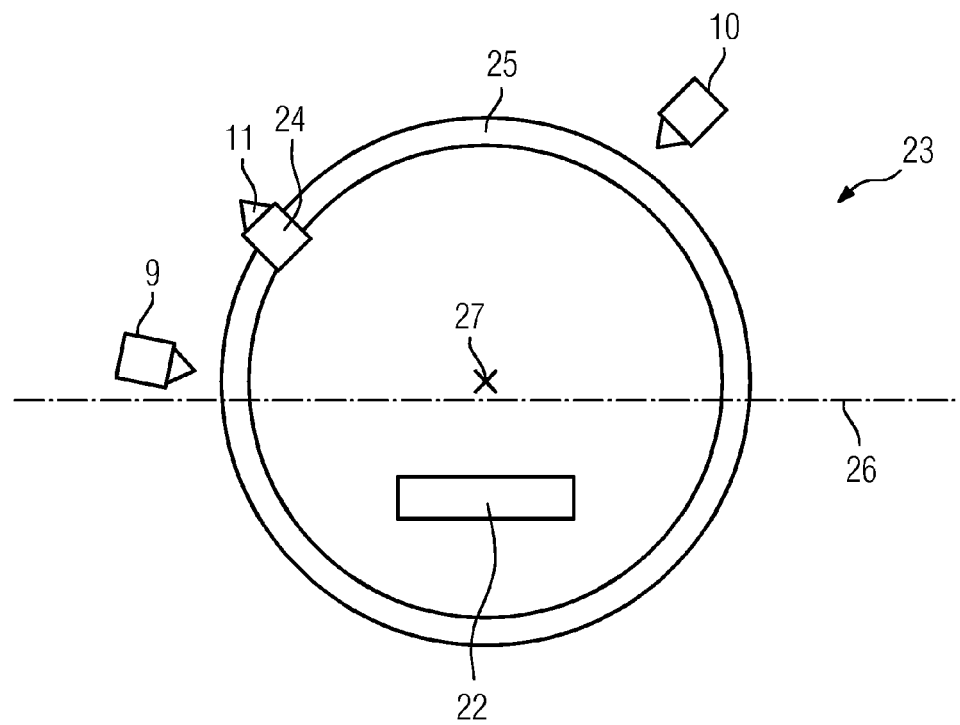
FIG. 5 shows one embodiment of a medical treatment device that includes a movement system.

FIG. 5 shows an example for using a movement system that uses a reference sensor and/or a calibration sensor in order to move an object with a high degree of accuracy into a reference position to move an object 24 about a predetermined axis 27. The movement system is part of a treatment device 23 (e.g., a unit for radiotherapy). The object 24 is a radiation source for providing radiotherapy to a patient who lies on the bed surface 22. The radiation source is guided along the guide rail 25 on a circular path around the axis 27. A movement of the object 24 is exclusively provided above the region marked by the line 26 shown as dashed-dotted lines. At the minimum angle (e.g., with a complete movement of the object 24 to the left), the object 24 is located in the reference volume and actuates the feeler of the reference sensor 9. The feeler of the calibration sensor 10 is actuated by the actuating element 11 of the object 24, with a rotation of approximately two thirds of the maximum rotational angle. A drive, not shown, is directly arranged on the object 24 and engages, via a mechanism, in teeth of the guide rail 25. A position of the object 24 may be determined, as explained in FIG. 1, with a high degree of accuracy from the alteration to the rotational angle of the drive shaft and an angular spacing between the reference sensor 9 and the calibration sensor 10 stored in a control device, not shown. Thus, a high degree of positional accuracy of the radiation source may be achieved in a treatment device.

Although the invention in detail has been illustrated and described more specifically by the exemplary embodiments, the invention is not limited by the disclosed embodiments. Other variants may be derived therefrom by the person skilled in the art, without departing from the protected scope of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A movement system for moving an object, the movement system comprising:
   a drive comprising a drive shaft;
   a mechanism that converts an alteration to a rotational angle of the drive shaft into an alteration to a position of the object;
   a rotational angle sensor operable to detect the alteration to the rotational angle;
   a reference sensor operable to emit a reference signal when the object enters a predetermined reference volume;
   a controller configured to communicate with the rotational angle sensor and the reference sensor, the controller being further configured to determine a total rotational angle from alterations to the rotational angle detected according to the reference signal and to activate the drive for rotating the drive shaft by a reference rotational angle determined as a function of a predetermined reference positional value and the total rotational angle; and
   a calibration sensor operable to emit a calibration signal when the object enters a predetermined calibration volume,
   wherein the controller is configured to store a current total rotational angle or a value derived therefrom when detecting the calibration signal as calibration information, and
   wherein the controller is configured to determine the reference rotational angle as a function of the calibration information.

2. The movement system of claim 1, wherein the reference sensor, the calibration sensor, or the reference sensor and the calibration sensor are each a feeler.

3. The movement system of claim 2, wherein an actuating element is provided on the object or fixed relative to the object, the actuating element actuating the respective feeler when the object enters the reference volume, when the object enters the calibration volume, or when the object enters the reference volume and when the object enters the calibration volume.

4. The movement system of claim 1, wherein the alteration to the position of the object is a linear movement between a first predetermined position and a second predetermined position.

5. The movement system of claim 4, wherein the reference sensor and the calibration sensor are arranged at a distance from one another, the distance being at least half of the distance between the first position and the second position.

6. The movement system of claim 1, wherein the alteration to the position of the object is a rotation about a predetermined axis between a first angular position and a second angular position.

7. The movement system of claim 6, wherein the reference sensor and the calibration sensor are arranged at an angular distance from one another, the angular distance being at least half of the angular distance between the first angular position and the second angular position.

8. The movement system of claim 1, wherein the controller is further configured to:
   store a predetermined positional value or a predetermined angular value that in each case describes the relative position of the calibration sensor to the reference sensor; and
   calculate the reference rotational angle, the calibration information, or the reference rotational angle and the calibration information as a function of the positional value, the angular value, or the positional value and the angular value.

9. A patient couch for a medical examination, treatment, or medical examination and treatment device, the patient couch comprising:
   a movement system for moving an object, the movement system comprising:
      a drive comprising a drive shaft;
      a mechanism that converts an alteration to a rotational angle of the drive shaft into an alteration to a position of the object;
      a rotational angle sensor operable to detect the alteration to the rotational angle;
      a reference sensor operable to emit a reference signal when the object enters a predetermined reference volume;

a controller configured to communicate with the rotational angle sensor and the reference sensor, the controller being further configured to determine a total rotational angle from alterations to the rotational angle detected according to the reference signal and to activate the drive for rotating the drive shaft by a reference rotational angle determined as a function of a predetermined reference positional value and the total rotational angle; and a calibration sensor operable to emit a calibration signal when the object enters a predetermined calibration volume, wherein the controller is configured to store a current total rotational angle or a value derived therefrom when detecting the calibration signal as calibration information, and wherein the controller is configured to determine the reference rotational angle as a function of the calibration information.

10. The patient couch of claim 9, wherein the reference sensor, the calibration sensor, or the reference sensor and the calibration sensor are each a feeler.

11. The patient couch of claim 10, wherein an actuating element is provided on the object or fixed relative to the object, the actuating element actuating the respective feeler when the object enters the reference volume, when the object enters the calibration volume, or when the object enters the reference volume and when the object enters the calibration volume.

12. The patient couch of claim 9, wherein the alteration to the position of the object is a linear movement between a first predetermined position and a second predetermined position.

13. The patient couch of claim 12, wherein the reference sensor and the calibration sensor are arranged at a distance from one another, the distance being at least half or at least two thirds of the distance between the first position and the second position.

14. The patient couch of claim 9, wherein the alteration to the position of the object is a rotation about a predetermined axis between a first angular position and a second angular position.

15. The patient couch of claim 14, wherein the reference sensor and the calibration sensor are arranged at an angular distance from one another, the angular distance being at least half or at least two thirds of the angular distance between the first angular position and the second angular position.

16. The patient couch of claim 9, wherein the controller is further configured to:

store a predetermined positional value or a predetermined angular value that in each case describes the relative position of the calibration sensor to the reference sensor; and calculate the reference rotational angle, the calibration information, or the reference rotational angle and the calibration information as a function of the positional value, the angular value, or the positional value and the angular value.

17. A method for operating a movement system for moving an object, the movement system comprising a drive, the drive comprising a drive shaft, the movement system further comprising a mechanism that converts an alteration to a rotational angle of the drive shaft into an alteration to a position of the object, a rotational angle sensor operable to detect the alteration to the rotational angle, a reference sensor operable to emit a reference signal when the object enters a predetermined reference volume, the movement system further comprising a controller configured to communicate with the rotational angle sensor and the reference sensor, the controller being further configured to determine a total rotational angle from alterations to the rotational angle detected according to the reference signal and to activate the drive for rotating the drive shaft by a reference rotational angle determined as a function of a predetermined reference positional value and the total rotational angle, the movement system further comprising a calibration sensor operable to emit a calibration signal when the object enters a predetermined calibration volume, wherein the controller is configured to store a current total rotational angle or a value derived therefrom when detecting the calibration signal as calibration information, and wherein the controller is configured to determine the reference rotational angle as a function of the calibration information, wherein when fulfilling a calibration condition, the method comprises:

activating, by the controller, the drive for moving the object until the object enters the reference volume;

setting the total rotational angle to zero;

activating the drive for moving the object until the object enters the calibration volume; and storing the current total rotational angle, a value derived from the total rotational angle, or the current total rotational angle and the value derived from the total rotational angle as calibration information.

18. The method of claim 17, wherein the fulfillment of the calibration condition is dependent on the time interval from when the method was last carried out.

* * * * *